United States Patent [19]
Novitski et al.

[11] Patent Number: 5,264,210
[45] Date of Patent: Nov. 23, 1993

[54] METHOD FOR PROTECTING PLANTS FROM NEMATODES USING P. CEPACIA STRAINS

[75] Inventors: Charles Novitski; Thomas J. McLoughlin, both of Madison, Wis.; Howard Atkinson, Leeds, England

[73] Assignee: Stine Seed Farm, Inc., Adel, Iowa

[21] Appl. No.: 214,301

[22] Filed: Jul. 1, 1988

[51] Int. Cl.$^5$ .................... A01N 63/00; A01C 1/06
[52] U.S. Cl. ................... 424/93 N; 47/57.6; 47/58
[58] Field of Search ............... 47/58, 57.605, 57.614, 47/58.13, 58.14, 57.6; 435/874, 252.34, 243, 252.1; 424/93, 93 N; 71/65

[56] References Cited

U.S. PATENT DOCUMENTS 4,798,723 1/1989 Dart et al. ........................ 424/93

OTHER PUBLICATIONS

Hickman, *Biology of the Invertebrates*, 2nd ed. The C. V. Mosby Co., Saint Louis, 1973, p. 256.
Mishra, et al. (1987) Journal of Industrial Microbiology 2: 267-276.
Suslow et al., EPO patent application 157,351, published Oct. 9, 1985.
Jaworski et al., EPO patent application 171,381, published Feb. 12, 1986.
Sayre (1980) Journal of Nematology 12: 260-269.
Hoitink, et al. (1986) Ann. Rev. Phytopathol. 24: 93-114.

*Primary Examiner*—Che S. Chereskin
*Attorney, Agent, or Firm*—Greenlee and Winner

[57] ABSTRACT

A method is provided for protecting a plant from nematodes and diseases associated with nematode invasion, which method comprises the step of inoculating said plant with a nematode-inhibiting strain of *P. cepacia* capable of colonizing said plant. The *P. cepacia* strain to be used should be non-pathogenic to said plant. Root inoculation of a plant with a nematode-inhibiting *P. cepacia* results in protection of the plant roots from nematode invasion. Foliar inoculation of the plant with these *P. cepacia* strains results in protection of the above-ground portions of the plant from nematode attack. Direct or indirect inoculation of seeds with nematode-inhibitory strains of *P. cepacia* strains can establish colonization of roots, stems and leaves of plants, and thus result in the protection of both roots and above-ground plant parts. The inoculum can be applied, for example, in the vicinity of a seed or young plant or it can be directly applied to a seed or to the above-ground parts of a young plant. Any plant colonized by the nematode-inhibiting *P. cepacia* of this invention may be protected against nematode attack. Specifically provided are two bacterial strains with inhibitory activity against plant-pathogenic nematodes: *P. cepacia* M36 (NRRL B-18379) and *P. cepacia* SG17 (NRRL B-18378).

11 Claims, 1 Drawing Sheet

Control

Number of Nematodes per Plant Root

P. cepacia M36

Number of Nematodes per Plant Root

METHOD FOR PROTECTING PLANTS FROM NEMATODES USING *P. CEPACIA* STRAINS

FIELD OF THE INVENTION

The present invention is in the field of biocontrol of nematodes and specifically relates to the control of plant pathogenic nematodes employing nematode-inhibiting strains of *Pseudomonas cepacia.*

BACKGROUND OF THE INVENTION

Nematodes are small wormlike animals, many of which are plant, animal or human parasites which cause a variety of diseases. Plant pathogenic nematodes are a major agricultural problem causing significant crop and yield losses. Plant tissue, particularly root tissue, is damaged by nematode feeding. Such feeding can cause mechanical tissue damage and the accompanying injection of nematode enzymes can cause further tissue disintegration. Nematode infections of roots result in root galls, and distortions in root growth. Similar symptoms accompany nematode infections of other parts of the plants. Important plant pathogenic nematodes include: root knot nematodes, Meloidogyne (e.g., *Meloidogyne incognita*); cyst nematodes Heterodera (e.g., *H. glycines, H. schachtii*) particularly for soybean and sugar beet; lesion nematodes Pratylenchus; burrowing nematodes *Radopholus similis;* stem and bulb nematodes Ditylenchus (e.g., *D. dipsaci*); citrus nematodes Tylenchulus; seed gall nematodes Anguina: and foliar nematodes Aphelenchoides.

Nematode infection can be accompanied by bacterial or fungal infection. In such plant-disease complexes, damage caused by nematodes can lead to enhanced severity of bacterial or fungal infection. For example, Fusarium and Verticillium wilts, Pythium damping off, Rhizoctonia and Phytophthora root rots as well as *Pseudomonas solanacearum* and *Corynebacterium insidiosum* bacterial wilts are enhanced by nematode infection. In addition, several nematodes (Xiphinema, Longidorus, and Trichodorus) are vectors for plant pathogenic viruses.

Plant pathogenic nematodes have been controlled by use of crop rotation or by the use of chemical fumigants and nematicides. In addition, a variety of nematode resistant plants have been developed using conventional breeding methods. Several methods of biocontrol have also been applied to plant pathogenic nematode control. A number of fungi, including *Verticillium chlamydosporium* and several bacteria, including *Bacillus penetrans* are reported to be effective against nematodes.

Miller and Sands (1977) J. Nematology 9:192-197 have reported that chitinase is toxic to certain nematodes. Chitin is a component of the cell wall of fungi, of nematode eggs and possibly present in nematcde larvae which is degraded by chitinase and other chitinolytic enzymes. The antimycolytic activity of soil bacterial isolates including strains of Bacillus, Pseudomonas and Arthrobacter have been associated with chitinase production (Mitchell and Alexander (1961) Nature 190:109-110; Sneh (1981) Phytopath. Z. 100:251-256). To applicants' knowledge, there have been no reports associating the nematode-antagonistic activity of bacterial soil isolates to chitinase production.

Suslow et al. EPO patent application 157351, published Oct. 9, 1985 describe a method for control of chitinase-sensitive plant pathogens, including nematodes, in which a rhizobacterium root-colonizing strain, for example *Pseudomonas fluorescens*, genetically altered to contain a chitinase gene, is employed as a plant inoculum. Jaworski et al. EPO patent application 171381, published Feb. 12, 1986 describe a method of nematode control using soil bacteria in which the bacteria are transformed to contain glycosidase enzymes and/or chitinase and thus to inhibit nematodes. Jaworski et al. also report that two *P. fluorescens* strains (701E1 and 112-12) isolated from soybean or corn roots inhibited infection of soybean or tomato plants by root knot nematodes. The mechanism by which the *P. fluorescens* isolates inhibited nematodes was not described.

Strains of *Pseudomonas cepacia* have been reported to produce a variety of antimicrobial compounds active against bacteria and/or fungi. *P. cepacia* ATCC 17759 is reported (German Patent No. 3149608, issued 1983) to produce substituted tropolones that are effective against bacteria and Streptococci. *P. cepacia* ATCC 39356 is reported (U.S. Pat. No. 4503218, issued 1985; Parker et al. (1984) J. Antibiot. 37:431–440) to produce Cepacin A and B, described as substituted furanones, which are effective as bactericides. Japanese patents 54-157501 (1979) and 55-122794 (1980) report "novel antibiotics" produced by *P. cepacia* strains BN 229-A and BN 225, respectively, which are effective against bacteria. Japanese Patent 53-127894 (1978) reports that *P. cepacia* strain KB-1 produces altericidin A, B and C which are effective against Eumycetes and effective against the causative agents of black spot of pear, gummy stem blight and scab of cucumber. *P. cepacia* ATCC 39277 is reported (U.S. Pat. No. 4,601,904, issued 1986) to produce xylocandin A and B which are active against yeast and fungi. *P. cepacia* strain 4137 is reported (Smirnov et al. (1982) Antibiotiki (Mosc.) 27:577–580) to produce a yellow pigment fraction, possibly a derivative of hydroxyphenazine carboxylic acid, which is active against bacteria, yeast and fungi. Pyrrolnitrin and aminopyrrolnitrin, which have antifungal activity, have been reported by Elander et al. (1968) Appl. Microbiol. 16:753–758, to be produced by *P. multivorans* (now included in the species *P. cepacia*). Recently these compounds have been reported to be produced by *Pseudomonas cepacia* strains having broad-spectrum antifungal activity (Dart et al. U.S. patent application Ser. No. 106,986 and Lambert et al. (1987) Appl. Environ. Microbiol. 53:1866-1871). Applicants know of no reports that associate the antimicrobial compounds produced by *P. cepacia* with nematode inhibition.

In several instances, *P. cepacia* strains have been reported to be useful for plant protection from plant pathogenic fungi. Kawamoto and Lorbeer (1976) Plant Dis. Reptr. 60:189–191 report that inoculation with *P. cepacia* strain 64–22 protected onion seedlings from damping off caused by a strain of *Fusarium oxysporum* f.sp. cepae. This *P. cepacia* was reported to be recovered from the root, root stem and seed coat of seedlings grown from inoculated seeds. *P. cepacia* 64–22 was, however, confirmed to be an onion pathogen itself. Becker et al. (1984) in *Proceedings of British Crop Protection Conference* (*Pests and Diseases*), Volume I, Nov. 19–22, 1984, BCPC Publications, Croyden, U.K. pp. 365–370 report that the *P. cepacia* strain of Kawamoto and Lorbeer, 1976, which they designate strain A4, is inhibitory in vitro to growth of a variety of fungi, including *Pythium ultimum, Rhizoctonia cerealis, Fusarium nivale* and *Ceratocystis ulmi* among others. Cavileer and Peterson (1985) Abstract No. 522, Phytopathological Society Annual Meeting report that inoculation with a strain of *P. cepacia* protected China Aster against wilt caused by *Fusarium oxysporum* f. sp. callistephi in greenhouse and field tests. Lumsden (1982) Phytopathology 72:709 reports that a strain of *P. cepacia* is antagonistic to the fungus *Pythium aphanidermatum* and can protect cucumber seedlings from infection. Lumsden and Sasser U.S. Pat. No. 4,588,584, issued May 13, 1986, describe the protection of cucumber and pea from Pythium disease employing seed inoculation with a new biotype of *P. cepacia* designated SDL-POP-S-1. Birch (1986) Australian Plant Pathol. 15:51-56 reports that *P. cepacia* isolates from the sugarcane rhizosphere strongly inhibited in vitro growth of *Pythium graminicola* but did not reduce disease in plant pot trials. Knudsen and Spurr (1987) Plant Dis. 71:442-445 report that leaf inoculation by a strain of *P. cepacia* controlled peanut leaf spot (*Cercospora arachidicola*). Elad and Chet (1987) Phytopathology 77:190-195 report that six bacterial strains, including a strain of *P. cepacia*, which were isolated from the rhizosphere of plants infested with Pythium were effective biocontrol agents for that fungus. Disease control was obtained in cucumber, bean, pepper, melon, tomato and cotton. It is also reported therein that suppression of disease is significantly correlated with competition for nutrients between the bacteria and germinating oospores of the fungus. Jones and Roane (1982) Can. J. Microbiol. 28:205-210 report that a strain of *P. cepacia* inhibited growth and spore formation of *Septoria nodorum*.

Becker et al. (1985) Med. Fac. Landbouww. Rijkuniv. Gent. 50/3b report the isolation of a number of bacterial isolates from the phytosphere of maize and chicory which are inhibitory to fungal growth in vitro. Fungal-inhibitory isolates included *P. cepacia, P. fluorescens, Erwinia serratia* and *Bacillus*. The Pseudomonas isolates are reported to display in vitro activity against a broad spectrum of fungi.

Dart et al. U.S. Pat. No. 4,798,723 describe a class of *P. cepacia* rhizosphere isolates designated *P. cepacia* type Wisconsin that are non-phytopathogenic, have broad spectrum antifungal activity, are able to colonize leaves and roots of a variety of plants and are able to protect plants which they colonize from fungal disease. These *P. cepacia* strains, exemplified by *P. cepacia* strain 526, were found to be active in vitro against several strains of *Fusarium, Sclerotinia sclerotiorum, Macrophomina phaseolina, Colletotrichum lindemuthianum* and *Rhizoctonia solani* among others.

While two rhizosphere isolates of *P. fluorescens* have been reported to inhibit nematode invasion (Jaworski et al., 1986), to applicants' knowledge there have been no reports that *P. cepacia* root isolates are effective for plant protection from nematode invasion.

SUMMARY OF THE INVENTION

It is an object of the present invention to provide a method for protecting plants from nematodes and diseases associated with nematode invasion. This method involves inoculating a plant with a nematode-inhibiting strain of *P. cepacia* which colonizes that plant. The method of this invention is based on applicants' discovery that a significant portion of the strains of *P. cepacia* isolated from the rhizosphere of plants display substantial inhibitory activity toward nematodes. Nematode inhibition is assessed herein in in vitro assays of bacteria-induced immobilization of nematodes, particularly *C. elegans* and *M. incognita*. Substantial inhibitory activity is defined as that which causes about 40% or greater nematode immobilization in in vitro agar plug assays. Strains of *P. cepacia* which display substantial nematode inhibitory activity and which colonize plants can protect those plants from nematode invasion. In a specific embodiment it has been found that nematode inhibitory strains such as *P. cepacia* M36 protect snap beans from the cyst nematode *H. glycines.*

A number of *P. cepacia* rhizosphere isolates are inhibitory to a broad spectrum of plant pathogenic fungi. While the nematode inhibitory activity of a strain is not necessarily correlated with antifungal activity, many *P. cepacia* rhizosphere isolates are inhibitory to nematodes and display broad-spectrum antifungal activity. *P. cepacia* rhizosphere isolates have been found to be active against fungi of the genera Fusarium, Sclerotinia, Rhizoctonia, Pythium, Macrophomina and Phytophthora, among others. Several strains of *P. cepacia* have been found to be highly inhibitory to nematodes, as well as being particularly effective against particular genera of fungi, for example Pythium, Sclerotinia and Rhizoctonia. In one specific embodiment, *P. cepacia* strain M36 is found to be both inhibitory to nematodes and particularly effective against strains of Pythium, particularly *Pythium ultimum*. In another specific embodiment, the nematode-inhibitory *P. cepacia* strain SG17 is also highly effective against strains of Sclerotinia and Rhizoctonia, particularly *Sclerotinia sclerotiorum* and *Rhizoctonia solani.*

Certain *P. cepacia* strains have been identified as pathogens of onion, garlic, orchid and alfalfa. Many of the *P. cepacia* rhizosphere isolates have been demonstrated to be non-pathogenic toward plants. The nematode-inhibitory *P. cepacia* strains employed in the method of the present invention should be non-pathogenic to the plant it is desired to protect. It is not necessary that the *P. cepacia* strains employed be non-pathogenic to all plants; however, the use of strains that are not plant-pathogenic is preferred.

Since the *P. cepacia* of the present invention colonize plant roots and/or stems and leaves, it is necessary that the inoculum be applied only in the vicinity of a seed or young plant, sufficiently closely that colonization is established. Root inoculation of a plant with nematode-inhibitory *P. cepacia* results in protection of the plant roots from nematode invasion. Foliar inoculation of the plant with these *P. cepacia* strains results in protection of the above-ground portions of the plant from nematodes. Direct or indirect inoculation of seeds with nematode-inhibitory strains of *P. cepacia* can establish colonization of roots, stems and leaves of plants, and thus result in protection of both roots and above-ground plant parts. Any plant colonized by the nematode-inhibiting *P. cepacia* of this invention may be protected against nematodes. For example, plant colonizing strains of *P. cepacia* have been found to be good colonizers of corn, sorghum, sunflower, cotton, pea, snap bean, oilseed rape, soybean, alfalfa, wheat, tomato, barley and African violets.

BRIEF DESCRIPTION OF THE FIGURE

FIGS. 1(*a*) and (*b*) are histograms showing the effect of *P. cepacia* strain M36 on the level of infection of snap bean roots by the cyst nematode *Heterodera glycines.* The graphs display the distribution of nematodes on plants, showing the number of plants having a certain number of nematodes. Results for control plants untreated (a) or for plants treated with *P. cepacia* M36 (b)

are shown. Following inoculation with M36, fewer plants have higher numbers of nematodes.

DETAILED DESCRIPTION OF THE INVENTION

Figure 1A:
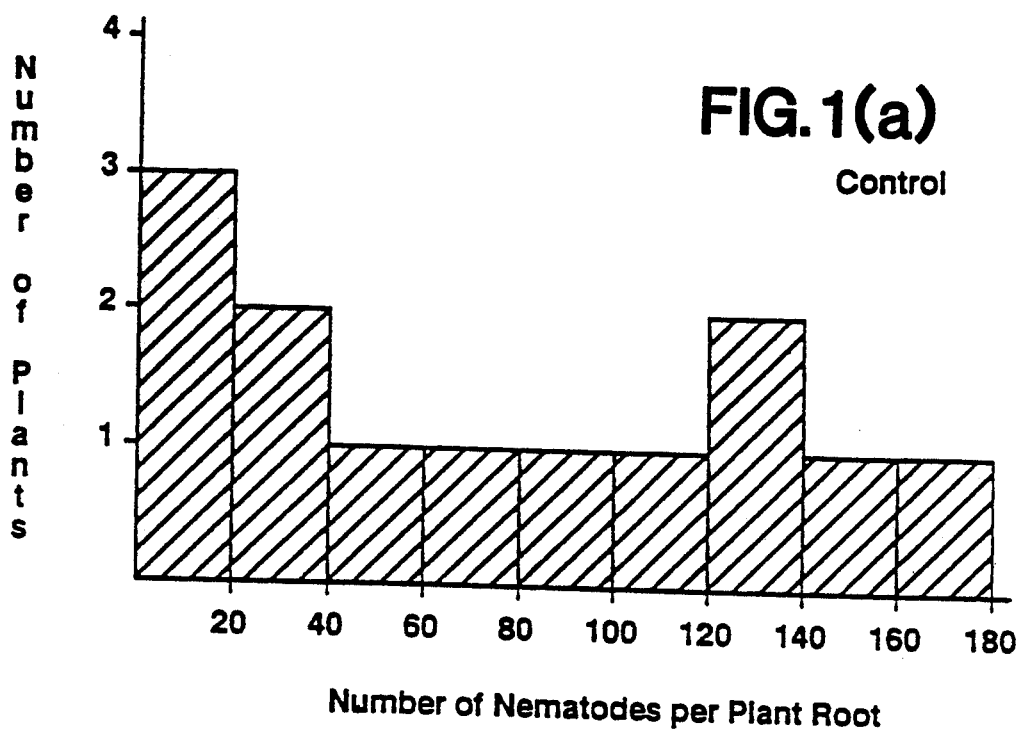

*Pseudomonas cepacia* are nutritionally diverse, nonfluorescent pseudomonads which can be identified by well established criteria summarized by Palleroni and Holmes (1981) Intl. J. System. Bacteriol. 31:479–481 and Palleroni (1984) in *Bergey's Manual of Systematic Bacteriology*, Vol. 1, Kreig (ed.) Williams and Wilkins, London pp. 140-199. Strains classified as *P. cepacia* include soil, plant and clinical isolates. Strains previously designated as *P. multivorans* (generally soil isolates) and *P. kingii* (generally clinical isolates) are now considered *P. cepacia*. Strains of *P. cepacia* can be reproducibly isolated from the environment by the use of selective media, such as PCAT medium (Burbage and Sasser (1982) Phytopathology 76:706) or more preferably TB-T medium (Hagedorn et al. (1987) Appl. Environ. Microbiol. 53:2265-2268), and identification of any particular strain as *P. cepacia* can be confirmed by conventional criteria, for example by use of the API-Zone Assay (Analytical Profile Index). In particular, strains of *P. cepacia* can be readily distinguished from fluorescent pseudomonads, such as *P. fluorescens*.

A number of *P. cepacia* plant isolates have been found to be plant pathogenic. *P. cepacia* strains have been associated with disease of onions and related plant species, such as garlic (Duranti et al. (1986) Orthofrutt. 70:289) and with brown spot of orchid leaves (Tsuchiya et al. (1986) Ann. Phytopathol. Soc. Jpn. 52:825-834). A bacterium resembling *P. cepacia* has also been reported to cause lesions in alfalfa stems and leaves (Lukezic (1974) Proc. Amer. Phytopath. Soc. 1:139). Dart et al. U.S. Pat. No. 4,798,723 reported that a number of *P. cepacia* rhizosphere isolates were not plant pathogens. Plant pathogenicity of *P. cepacia* isolates can be assessed in pathogenicity assays which include positive (recognized pathogens) and negative (non-pathogens) control strains of *P. cepacia*. For example onion pathogenicity can be assayed by inoculating white onion tissue with test cultures as described in Cother and Dowling (1985) Austral. Plant Pathol. 14:10-12, and in U.S. Pat. No. 4,798,723. In such assays, white onion (bulb) tissue is inoculated with a bacterial culture, inoculated tissue is incubated for up to 72 hr and examined for discoloration. Pathogenicity is assessed by comparing test inoculated tissue with tissue inoculated with known pathogens, for example *P. cepacia* strain 64-22 (Kawamoto and Lorbeer, 1976 supra) is a positive control for onion pathogenicity assays. Similar assays can be employed to assess pathogenicity to other plants. A strain that is pathogenic to one type of plant is not necessarily pathogenic to other types of plants. Furthermore, different pathogenic strains can display varying levels of virulence toward a plant. While it is preferred that the nematode-inhibitory *P. cepacia* employed in the method of the present invention are not pathogenic to plants, this is not an absolute requirement. It is only necessary that the strain employed as a protective inoculum of a plant is not pathogenic to that plant.

Dart et al. U.S. patent application Ser. No. 106,986 report that a number of *P. cepacia* strains isolated from corn root tissue and corn rhizosphere were good colonizers of the roots and rhizosphere of corn. In addition, the corn root-colonizing strains of *P. cepacia* were found to also be good colonizers of the roots and rhizosphere of a variety of other plants, including sorghum, sunflower, cotton, pea, barley and African violets. The *P. cepacia* which were good colonizers of the rhizosphere of plants were also found to colonize leaves of a variety of plants. Colonizing ability of a particular strain on a plant can be assessed by measuring the persistence of that strain after inoculation of the plant. For example, a test bacterium carrying a selectable or screenable marker, such as rifampicin resistance, is inoculated onto a plant (roots, leaves or seeds) and the number of the marker bacteria recoverable from the plant is measured with time usually by plating on a selective medium (i.e. rifampicin containing medium). Often the number of marked strains recovered is compared to the total bacteria recovered, which can be measured for example by plating on a non-selective medium such as nutrient agar. The absolute number of bacteria recoverable from a plant will depend on the level of inoculum used, the method of inoculation and the plant growth conditions. The *P. cepacia* strains of the present invention are considered to be good colonizers if they are recoverable from inoculated plants, up to about two weeks after inoculation, at a level greater than or equal to about 1% of the total bacterial population.

A number of *P. cepacia* strains have been identified as being inhibitory to growth of fungi (vide supra). For example, U.S. Pat. No. 4,798,723 describes a distinguishable type of *P. cepacia* designated *P. cepacia* type Wisconsin which has the combined characteristics of good colonization of plant roots and leaves, nonpathogenicity (as measured toward onions), broad-spectrum in vitro fungal antagonism and the ability to protect plants from infection and invasion by fungi. In related work, *P. cepacia* isolated from the rhizosphere and/or roots of several plants have been found to be broad-spectrum fungal antagonists, and to display significantly improved activity against particular fungi or groups of fungi. For example, *P. cepacia* isolates having particularly strong antagonism to Sclerotinia and Rhizoctonia (*P. cepacia* SG17) and strains having strong antagonism to Pythium (*P. cepacia* M36) have been identified. These particularly strong fungal antagonists have also been demonstrated to protect plants that they colonize from fungal infection.

A particular *P. cepacia* isolate can be assessed for fungal antagonism using in vitro plate assays as has been described in U.S. Pat. No. 4,798,723, which is incorporated by reference herein. Such assays involve inoculating the outer edge of an agar plate containing an appropriate growth medium, such as potato dextrose agar, with the test bacterial isolate. The center of the plate is then inoculated with a fungal culture. The test plates and appropriate controls are then incubated for up to about 14 days and examined throughout this time for inhibition of fungal growth. Quantitative comparisons of fungal antagonism by different strains of bacteria can be made by measuring the zone of fungal growth inhibition around the site of bacterial growth with larger zones of inhibition indicating stronger antagonism.

The present invention is based on applicants' discovery that a significant portion of *P. cepacia* isolates obtained from plant rhizosphere (root and/or soil) samples displayed in vitro inhibition of nematodes. Inhibition was assessed as nematode immobilization in agar plug assays. Among strains that effected nematode immobilization above background levels (less than or equal to about 5% immobilization), almost 40% of the strains displayed substantial inhibition (greater than or equal to about 40% immobilization). Applicants also discovered that a high proportion of strains having substantial nematode inhibition were also fungal antagonists, although there appears not to be a quantitative, direct correlation between fungal and nematode antagonism. Applicants have also demonstrated that in vitro assays for nematode inhibition employing one species of nematode (i.e., *C. elegans*) are predictive of nematode inhibition against other nematodes (i.e., *H. glycines* and *M. incognita*) at least for those strains displaying immobilization above about 40%. Applicants have further demonstrated that in vitro nematode immobilization assays are predictive of the ability of a strain to be useful for protection of plants against nematode invasion. Strains employed for plant protection must, however, also colonize the plant that it is desired to protect.

In an initial screening procedure, 212 strains of *P. cepacia*, most of which were rhizosphere isolates, were tested for nematode inhibition in in vitro plate assays. Initial screening was done by assessing the ability of the bacterial isolates to produce substances that were inhibitory to the soil nematode *C. elegans*. Nematode inhibition was assessed by determining the number of nematodes immobilized after exposure to agar plugs taken from the areas surrounding bacterial colonies grown on agar plates. Those *P. cepacia* strains which exhibited over 40% nematode immobilization in initial screening were considered to be nematode-inhibiting strains. Of the original *P. cepacia* strains tested, 57% displayed no nematode inhibitory activity (less than about 5% immobilization), 26% displayed weak inhibition (between about 5–40% immobilization) and 17% displayed substantial inhibition (greater than about 40% immobilization).

The thirty six strains initially identified as being substantially inhibitory to *C. elegans* were retested using agar plug assays for inhibition of the plant pathogenic nematode *M. incognita* as well as *C. elegans*. The results of these assays, given in terms of the percent worms immobilized, are presented in Table 1. All of the strains retested, except one (MB46), were again found to immobilize over 40% of the nematodes. In general, the immobilization results are quantitatively consistent for different species of nematode. Therefore, the results of nematode inhibition assays using *C. elegans* can be employed, in general, to assess inhibitory activity toward other nematodes. This correlation is particularly good for those bacteria having strong immobilization activity.

A number of the *P. cepacia* isolates that were tested for nematode inhibition were also tested for fungal antagonism. The results of in vitro antifungal assays of a number of *P. cepacia* isolates against several strains of fungi are presented in Table 2. The results of Table 2 are relative and qualitative, based on a comparison of the size of zones of fungal growth inhibition. A "−" means no inhibition, a "+" means moderate inhibition, "+++" or higher means strong inhibition; in general, the greater the number of "+", the larger the zone of inhibition. All of the isolates in Table 2 were tested for nematode inhibition; however, some displayed inhibition levels below the cut-off value (40%) for the initial screening and so are not listed in Table 1. Those not listed in Table 1 had the following nematode-inhibition ratings: P1, P6, J81, all less than 5% (background); *P. cepacia* type Wisconsin 526, 18%; and J51, 20%.

In addition to the *P. cepacia* rhizosphere isolates, several known *P. cepacia* strains, available from the American Type Culture Collection (ATCC) 12301 Parklawn Drive, Rockville, Md., were tested in agar plug assays using *C. elegans* for nematode inhibition. The following ATCC strains were tested: ATCC 25416, an onion pathogen; ATCC 17460; ATCC 17616; ATCC 39277, a cornfield isolate which produces the antifungal agents xylocandins (U.S. Pat. No. 4,601,904); ATCC 29424; and ATCC 10856. None of the ATCC strains tested affected nematode immobilization above the 40% level. Only two of the ATCC strains tested affected nematode immobilization above the 5% level: ATCC 39277, 31% immobilization and ATCC 29424, 16% immobilization.

Comparison of fungal antagonism and nematode inhibition assays of Tables 1 and 2 indicate that there is not a general, direct correlation between the two properties. This suggests that the mechanism of fungal inhibition is not the same as that of nematode inhibition. For example, isolate P6, which is moderately active against fungi (compared to the other strains tested), shows no nematode immobilization above background. Similarly, J51, having strong activity against Sclerotinia and Rhizoctonia, is not strongly active for nematode immobilization. Furthermore, the strength of antifungal activity is not necessarily correlated with the strength of nematode inhibition. For example, strain J14 appears to be moderately stronger in activity against fungi than strain J9, but J14 appears to be less active than J9 against nematodes. Not all strains of *P. cepacia* that are strong fungal antagonists are also substantially inhibitory to nematodes; however, all of the strains of nematode-inhibitory *P. cepacia* listed in Table 1 and strain SG17 have been found to display antagonism toward at least one strain of fungus.

The mechanism of nematode inhibition is not known; however, based on the assay methods used, in vitro inhibition is expected to be associated with the release of one or more nematode-inhibitory compounds by the *P. cepacia* strains. None of the antimicrobial and/or antifungal compounds reported to be released by various strains of *P. cepacia* have been identified as antagonistic toward nematodes.

It is known (Dart et al. U.S. Pat. No. 4,798,723) that a significant number of *P. cepacia* rhizosphere isolates are good colonizers of plant roots and/or rhizosphere. In particular, *P. cepacia* strain M36 was found to be a good colonizer of the roots and rhizosphere of a variety of plants. The ability of nematode-inhibitory *P. cepacia* strains to protect plants from nematode invasion was assessed in growth chamber experiments. Specifically, the ability of inoculation by *P. cepacia* strain M36 to protect the roots of snap bean seedlings from invasion by the cyst nematode *H. glycines* was examined. The results of plant protection assays are summarized in Table 3 and plotted in FIG. 1. In the absence of the *P. cepacia* M36 inoculum, the number of nematodes/root ranged from 0 to 174, with a mean of 79 $\pm$61. On bean seedlings inoculated with strain M36, the number of nematodes/root ranged from 0 to 91, with a mean of 38$\pm$28. *P. cepacia* M36 has been placed on deposit with The Northern Regional Research Laboratory, 1815 North University Street, Peoria, Ill. 61604, and given accession number NRRL B-18379. *P. cepacia* M36 is also a strong antagonist of Pythium fungal strains.

The rhizosphere and roots of M36-inoculated 16-day-old snap bean plants were sampled for the presence of *P. cepacia* using PCAT medium. *P. cepacia* M36 was present in these samples at a level of $2\times10^7$ to $2\times10^8$ cells/- gram sample, which represented about 10% of the total bacterial population (assessed by plating on nutrient agar) present.

*P. cepacia* SG17 has been found to be a strong antagonist of Sclerotinia and Rhizoctonia, and to have the ability to protect plants from infection by these fungi. This strain has also been found to be a good colonizer of the roots and rhizosphere of a variety of plants. As noted above, *P. cepacia* SG17 is also inhibitory to nematodes. *P. cepacia* SG17 has been placed on deposit with The Northern Regional Research Laboratory, 1815 North University Street, Peoria, Ill. 61064, and given accession number NRRL B-18378.

A primary use of the bacteria in the present invention is the inoculation of a plant to protect that plant from nematode invasion and plant diseases associated with nematode invasion. Since the bacteria of the present invention are colonizers of plants, it is only necessary that they be applied in the vicinity of the seed or young plant, sufficiently close to establish colonization. It is preferred that the bacterial strains of the present invention be applied in the vicinity of the seed at the time of planting in order to establish root colonization. This can be accomplished by either direct or indirect inoculation of seeds at the time of planting. A single nematode-inhibitory strain or mixtures of two or more strains can be employed for inoculation.

By direct inoculation is meant that the bacterial inoculant is applied directly to the seed prior to sowing it in the field. In its simplest form, this can be done by spraying the seed with or dipping the seed into a liquid culture containing a strain of the present invention. This results in a plant seed coated with a composition containing the bacterium. A preferred method of direct inoculation is to pellet the seed with a carrier containing the desired *P. cepacia* strain. Generally, the bacterium is applied to a carrier and then a pellet is formed with the carrier surrounding the seed. Numerous, diverse carriers are known to those of ordinary skill in the art and include, but are not limited to, peat, soil, calcium carbonate (many forms), dolomite, gypsum (various grades), bentonite (and other clay minerals), rock phosphates (and other phosphorous compounds), titanium dioxide, humus, talc, alginate and activated charcoal. Any agriculturally suitable carrier known to one skilled in the art would be acceptable. Often, it is desirable to include an adhesive in the pellet to hold the bacterium-containing carrier to the seed. While the art is also aware of numerous acceptable adhesives, some of them include, but are not limited to, synthetic glues, glues of vegetable origin (such as gum arabic), gelatin, various sugars, and bee honey. In general, the solid carrier should be close to neutral pH and finely ground (i.e., at least about 90% passing through 300 mesh). Pelleted seed containing the microorganism of the present invention can be directly sown in the field. Clearly inoculum components must not affect bacterial or plant growth.

A typical inoculant employed in the present invention is prepared by mixing gum arabic (30% w/v) with the bacterial strain in a finely ground (to pass 300 mesh) peat carrier. This mixture is then mixed with seed.

An alternative to direct seed inoculation is indirect seed inoculation; i.e., an agricultural inoculum containing a bacterium of the present invention in a suitable carrier is introduced into the vicinity of the seed at the time of sowing. The carrier can either be solid or liquid, many being known to those of skill in the art. The basic requirement is that the carrier neither be phytotoxic, bacteriostatic, nor bacteriocidal. An example of a liquid agricultural inoculum is simply a *P. cepacia* strain of the present invention in a liquid growth medium, which is sprayed into the row as the seed is planted. Solid carriers can comprise many of the materials indicated as being suited for pelleting seed. For example, a popular method is to employ peat suspended in water as a carrier of the bacterium, and spray this mixture into the row in the furrow beside and over the seed as it is planted. Another example of a solid agricultural inoculum is granules comprised of calcium sulfate hemihydrate and carboxymethylcellulose sprayed with a bacterial broth. Yet another example of a solid inoculant is granulated peat inoculated with a bacterium which is run into the seed furrow at planting in the vicinity of the seed. Other examples of solid inoculant are quartz sand and marble chips coated with a peat culture of the bacterium. It is also known to include nutrients, such as powdered milk or sucrose, in the solid inoculant granules. Similar inocula can be applied in the vicinity of the roots of young plants.

Among the *P. cepacia* strains of the present invention are those that colonize the above-ground surface of plants, i.e. leaves and stems. These strains can be employed to protect plant stems and leaves from nematode damage. In order to establish a leaf-colonizing strain on leaf tissue, it is necessary to inoculate leaves with an appropriate agricultural composition containing the desired strain. Such foliar inoculants can be applied, in principle, at any time during growth of the plant. A particularly useful method of inoculating plant leaves is by spraying, either liquid or particulate inoculating compositions onto plant leaves.

Inoculating compositions suitable for spraying generally include a sprayable agricultural carrier such as water which contains viable cells of the desired bacterial strain. Often, it is desirable to include wetting, emulsifying and sticking agents to improve application. It may be desirable also to include bacterial nutrients or other additives which enhance retention of inoculum viability. Again, all components of such a composition must be non-toxic to plants and the bacterial inoculant, and further must not inhibit bacterial growth (bacteriostasis) or injure plant foliage.

The present invention contemplates that those of ordinary skill in the art are familiar with the basic techniques of agricultural inoculation. See, e.g., Brockwell in *Methods for Evaluating Biological Nitrogen Fixation*, pp. 417-488 (F. J. Bergersen, ed., 1980); Burton in *Biological Nitrogen Fixation Technology for Tropical Agriculture*. pp. 105-114 (P. H. Graham and S. Harris, eds. 1982); Roughley, Ibid., pp. 11-127; Brockwell in *Nitrogen Fixation in Legumes*, p. 211-227 (J. M Vincent, ed., 1982); Kremer et al., (1982) Soil Sci. Soc. Am. J. 46:539-542; Kremer et al., (1983) Appl. Env. Microbiol. 45:1790-1794; Brockwell (1962) Aust. J. Agr. Res. 13:638; Bergersen et al. (1958) J. Aust. Inst. Agric. Sci. 24:158; Hastings et al. (1962) N.Z. J. Agr. 104:330; Fraser (1966) J. App. Bacteriol. 29:587; Schiel et al. (1970) Rev. Invest. Agropec. Ser. 7:239; Iswaran et al. (1971) Zentralbl. Bakteriol. Parasitenk. Infektionskr., Abt. II 126:43,45.

Nematode-inhibitory *P. cepacia* strains suitable for use in the methods of the present invention can be readily and reproducibly identified by those of ordinary skill in the art by application of the assay and selection methods described herein. Any *P. cepacia* rhizosphere isolate or other known *P. cepacia* strain can be tested as described in Example 2 for nematode inhibition. Such tests can include known positive (i.e., strain M36) or negative (i.e., ATCC 10856) controls. Nematode-inhibitory strains can be tested for plant colonizing ability by conventional techniques as described herein. It is recommended that plant-colonizing, nematode-inhibitory *P. cepacia* strains be tested in greenhouse or field tests for plant protection, as has been described herein. The nematode inhibitory *P. cepacia* strains of the present invention can also be readily assayed using conventional in vitro plate assays for antifungal activity.

The following examples are included for illustrative purposes only and are not intended to limit the scope of the invention. Since modification of the examples below will be apparent to those of skill in the art, it is intended that this invention be limited only by the scope of the appended claims.

EXAMPLE 1:

ISOLATION OF *Pseudomonas cepacia* Strains

*Pseudomonas cepacia* strains were isolated from soil or root samples taken from corn, sorghum or barley fields. Alternatively, *P. cepacia* strains were isolated from roots of corn, sorghum or barley seedlings grown in field soil samples. Samples were prepared as described in Dart et al. U.S. Pat. No. 4,798,723 and the resulting soil suspensions, root washings or root macerate solutions were serially diluted and plated on a *P. cepacia* selective medium such as PCAT (Burbage and Sasser, 1982, supra) or more preferably TB-T medium (Hagedorn et. al., 1987, supra). Individual colonies of *P. cepacia* rhizosphere isolates were selected from these plates and repurified. The purified *P. cepacia* rhizosphere isolates were then tested in nematode inhibition assays. Any *P. cepacia* strain, obtained from public or private culture collections, can also be tested for activity in nematode inhibition assays.

EXAMPLE 2

Nematode Inhibition Assays

Root knot nematodes, *Meloidogyne incognita* (obtained from R. Hussey, University of Georgia, Athens, Ga.) were propagated on tomatoes (*Lycopersicon esculentum* Mill. "Rutgers"). Eggs were collected from roots after sodium hypochlorite treatment and hatched at 25° C. in tap water. The nematode eggs were collected by centrifugation in 40% sucrose at 2000×g for 5 minutes.

The soil nematode, *Caenorhabditis elegans*, was maintained on a lawn of *Escherichia coli* OP50-1 (Str$^R$, c80 phage resistant, Ura$^-$, obtained from C. Johnson, University of Wisconsin, Madison, Wis.) on NG agar plates at 20° C. as described by Brenner (1974) Genetics 77:71-94. The worms were harvested from plates into M9 medium (Brenner, 1974, supra) and smaller worms were selected by filtration through a 10 μm nylon filter.

Potato dextrose broth (PDB, Difco) was inoculated with the bacterial isolate to be tested and the culture was grown overnight at 30° C., after which 20 μl aliquots of the liquid culture were applied to Potato dextrose agar (PDA, Difco). The inoculated plates and uninoculated controls were incubated at room temperature for about 7-34 days exposed to daylight. Alternatively, plates were incubated at 30° C. for one day prior to room temperature incubation. After incubation, agar plugs (1.1 cm diameter) were taken from the plates and transferred to empty petri dishes. The plugs were taken from areas of the plate that were near to, but did not include, bacterial colonies on the plates. Nematodes were then placed on the surface of the agar plugs. Either freshly hatched *M. incognita* juveniles (8 μl, approximately 160 worms) or *C. elegans* (5 μl, approximately 200 worms) which had been passed through a 10 μm filter were added to agar plugs. The agar plates inoculated with nematodes were stored in moist pouches at 20° C. in the dark for 20 hours, after which the percentage of worms that were motionless was determined.

A time course study of nematode inhibition as a function of incubation time of the bacterial plates from which agar plugs were taken was performed. This study examined production of nematode inhibitory substance(s) as a function of bacterial incubation time. Agar plugs were taken after 1, 2, 3, 6, 12, 24, 31 and 48 days of room temperature incubation and tested for nematode immobilization. In general, nematode immobilization activity peaked at 12 days of bacterial incubation. Both M36 and SG17 showed maximal immobilization activity at 12 days in these time courses.

EXAMPLE 3

Plant Protection Assays

The soybean cyst nematode, *Heterodera glycines*, was collected from soybean root cysts and juveniles were obtained as described by Atkinson et al. (1988) Ann. Appl. Biol. 112:459-469.

Figure 1B:
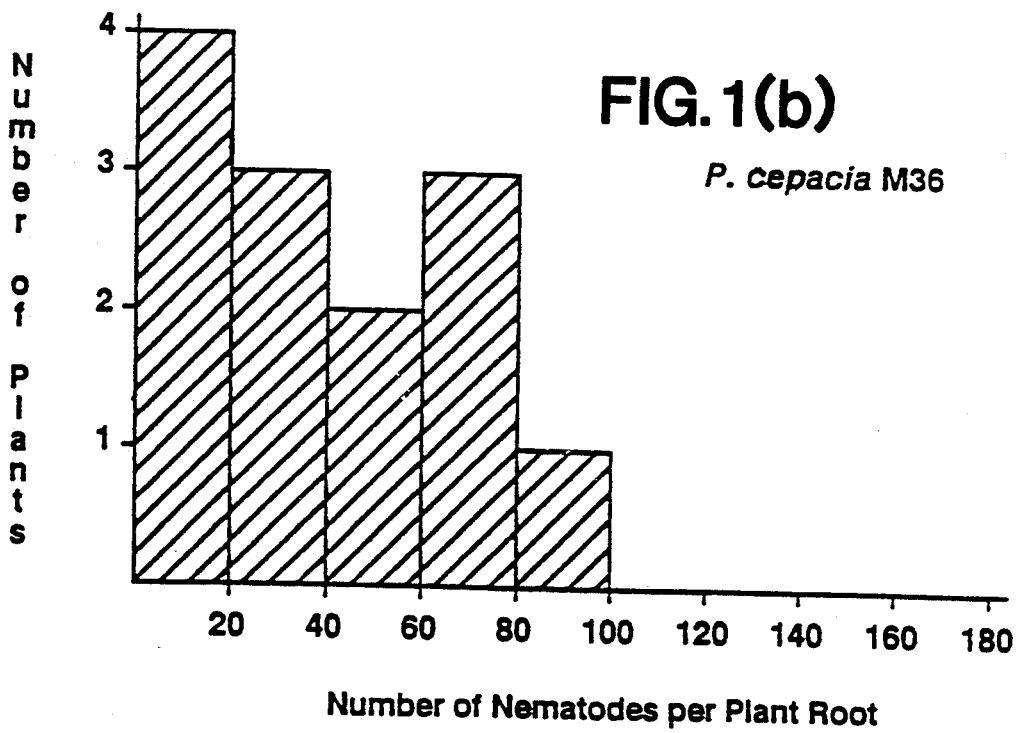

Three day old snap bean (*Phaseolus vulgaris*) seedlings were transferred to moist sand (mesh 50-70) in 100 ml plastic cups set within a 4 tier Magenta box enclosure arranged with a cotton wick extending from the sand cup in the top tier to a reservoir of tap water in the lower tier. The box was designed such that there was about a 60% moisture level in the sand initially to provide moisture during the course of the experiment. On the day of seedling transfer, the growth chamber was maintained at 25°-30° C. Half of the seedlings were inoculated with a culture of the test bacterium. Typically, 1 ml of an overnight culture grown in PDB (about $10^9$ cells/ml) was pelleted and resuspended in water and applied to the roots of seedlings. When the seedlings were 10 days old, *H. glycines* juveniles (hatched within the last week) were inserted into the planting sand. The nematodes (25 worms/g sand) were placed in 3 equidistant holes (about 3 cm deep, spaced about 4 cm from the base of the plant stem) around the seedling in order to distribute the nematodes around the plant roots. Seedlings were harvested at 16 days. Samples of roots subjected to each treatment were sacrificed in order to assess the rhizosphere bacterial population by plating root macerate on PCAT and NA medium. The remaining roots of test and control plants were weighed, stained by acid fuchsin (Byrd et al. (1983) J. Nematol. 15:142-143) and the number of nematodes that had entered the root system was determined by microscopic examination of the stained tissue. Results are reported in Table 3 and FIG. 1 as the number of nematodes/gram of root and nematodes/root.

TABLE 1

The effect of *Pseudomonas cepacia* strains on mobility of the root knot nematode, *M. incognita*, and the soil nematode, *C. elegans*.

| *P. cepacia*[1] Strain | Percent of worms immobilized[2] | |
|---|---|---|
| | *M. incognita* | *C. elegans* |
| No Bacteria | 3.4 | 6.1 |

TABLE 1-continued

The effect of Pseudomonas cepacia strains on mobility of the root knot nematode, M. incognita, and the soil nematode, C. elegans.

| P. cepacia[1] Strain | Percent of worms immobilized[2] | |
|---|---|---|
| | M. incognita | C. elegans |
| M36 | 97.9 | 89.3 |
| MB19 | 93.8 | 92.9 |
| MB6 | 91.4 | 87.5 |
| MB43 | 91.0 | 76.8 |
| MB14 | 89.3 | 89.2 |
| MB23 | 88.9 | 97.8 |
| MB21 | 88.4 | 98.7 |
| MB17 | 87.0 | 100.0 |
| MB4 | 86.7 | 91.8 |
| MB34 | 85.8 | 77.1 |
| MB56 | 85.7 | 88.5 |
| M37 | 84.6 | 82.4 |
| M54 | 82.4 | 75.0 |
| MB51 | 82.2 | 71.1 |
| M52 | 81.6 | 60.3 |
| J9 | 81.4 | 87.0 |
| MB20 | 80.1 | 84.9 |
| M53 | 79.8 | 57.1 |
| MB47 | 76.3 | 69.9 |
| MB18 | 76.2 | 88.1 |
| J8 | 75.5 | 93.6 |
| MB12 | 72.8 | 89.3 |
| J3 | 71.2 | 85.9 |
| MB24 | 70.5 | 89.5 |
| MB42 | 70.5 | 45.6 |
| MB8 | 70.5 | 76.2 |
| MB13 | 70.2 | 82.7 |
| M55 | 66.4 | 79.6 |
| MB6 | 65.9 | 48.0 |
| MB54 | 65.8 | 62.1 |
| JB8 | 64.1 | 75.3 |
| SG17 | NT | 62.0 |
| MB52 | 59.5 | 68.8 |
| M51 | 58.2 | 75.4 |
| MB16 | 54.4 | 53.9 |
| J14 | 54.1 | 73.8 |
| MB46 | 37.4 | 33.7 |

[1] J and JB isolates are from corn field soil Prescott, WI; M and MB isolates are from the Morrow (corn field) plots, Illinois; SG isolates are from Spring Green, WI soil.
[2] Data were obtained as described in Example 2 with bacterial plants incubated for 33 days; SG17 results are from time course data, see Example 2, measured with bacterial plates incubated for 31 days; NT = not tested.

TABLE 2

In vitro fungal antagonism of P. cepacia rhizosphere isolates

| Isolate No.[1] | Sclerotinia sclerotiorum | Pythium | Rhizoctonia solani | Fusarium moniliforme |
|---|---|---|---|---|
| M36 | ++ | +++++++ | + | ++ |
| M37 | − | +++++ | − | + |
| J3 | ++ | + | + | +++ |
| J8 | ++ | + | + | +++ |
| J9 | ++ | + | + | +++ |
| J14 | +++ | + | +++ | +++ |
| P6 | +++ | + | ++ | ++ |
| P1 | − | − | − | − |
| J51 | ++++++ | + | +++++++ | + |
| J81 | +++ | + | + | ++ |
| SG17 | +++ | + | +++ | +++ |
| 526 | ++ | + | + | + |
| ATCC 29424 | +++ | + | ++++ | + |
| ATCC 25416 | − | + | + | − |
| ATCC 39277 | ++ | +++ | ++++ | +++ |
| ATCC 10856 | − | − | − | − |

[1] J isolates are from corn field soil Prescott, WT; M isolates are from corn field soil, Morrow plots, Illinois; P isolates are from Prescott WI corn field soil, stored for about 3 years prior to testing. SG isolates from Spring Green, WI soil.

TABLE 3

The number of nematodes infecting snap bean roots in the absence (2a) and the presence (2b) of Pseudomonas cepacia strain M36.

| Plant | Nematodes per Root | Root Weight (g) | Nematodes per Gram of Root |
|---|---|---|---|
| 2a | | | |
| 1 | 138 | 0.31 | 445 |
| 2 | 146 | 0.22 | 664 |
| 3 | 98 | 0.31 | 316 |
| 4 | 76 | 0.31 | 245 |
| 5 | 138 | 0.52 | 265 |
| 6 | 0 | 0.39 | 0 |
| 7 | 118 | 0.26 | 454 |
| 8 | 12 | 0.14 | 85.7 |
| 9 | 174 | 0.45 | 387 |
| 10 | 0 | 0.27 | 0 |
| 11 | 37 | 0.42 | 88.1 |
| 12 | 59 | 0.36 | 164 |
| 13 | 25 | 0.32 | 78.1 |

For the number of nematodes/root: $\bar{x} = 79$, sd $= 61$.
For the number of nematodes/gram of root: $\bar{x} = 246$, sd $= 202$.

| | | | |
|---|---|---|---|
| 2b | | | |
| 1 | 11 | 0.48 | 22.9 |
| 2 | 46 | 0.66 | 69.7 |
| 3 | 69 | 0.20 | 345 |
| 4 | 36 | 0.37 | 97.3 |
| 5 | 23 | 0.15 | 153 |
| 6 | 44 | 0.37 | 119 |
| 7 | 66 | 0.29 | 228 |
| 8 | 6 | 0.54 | 11.1 |
| 9 | 23 | 0.30 | 76.7 |
| 10 | 91 | 0.23 | 396 |
| 11 | 1 | 0.49 | 2.04 |
| 12 | 64 | 0.30 | 213 |
| 13 | 11 | 0.21 | 52.4 |

For the number of nematodes/root: $\bar{x} = 38$, sd $= 28$.
For the number of nematodes/gram of root: $\bar{x} = 137$, sd $= 125$.

We claim:

1. A method for protecting a plant from a plant pathogenic nematode species which comprises the step of inoculating said plant with a strain of P. cepacia which strain colonizes said plant, and which strain is effective to immobilize at least about 40% of said nematodes in in vitro agar plug assays.

2. The method of claim 1 wherein said inoculating step comprises inoculating the roots of said plant.

3. The method of claim 1 wherein said inoculating step comprises applying said nematode-inhibiting strain of P. cepacia to a seed of said plant.

4. The method of claim 1 wherein said nematode-inhibiting strain of P. cepacia is a rhizosphere isolate.

5. The method of claim 1 wherein said nematode-inhibiting strain of P. cepacia displays broad-spectrum anti-fungal activity.

6. The method of claim 1 wherein said nematode-inhibiting strain of P. cepacia displays activity against fungi of the genus Pythium.

7. The method of claim 1 wherein said nematode-inhibiting strain of P. cepacia displays activity against fungi of the genus Sclerotinia.

8. The method of claim 1 wherein said nematode-inhibitory strain of P. cepacia displays activity against fungi of the genus Rhizoctonia.

9. The method of claim 1 wherein said nematode-inhibiting strain of P. cepacia is not pathogenic to plants.

10. The method of claim 1 wherein said nematode-inhibiting strain of P. cepacia is P. cepacia M36.

11. The method of claim 1 wherein said nematode-inhibiting strain of P. cepacia is P. cepacia SG17.

* * * * *